Nov. 12, 1957 J. G. VALDREZ Plant Pat. 1,660
ROSE PLANT
Filed March 19, 1957
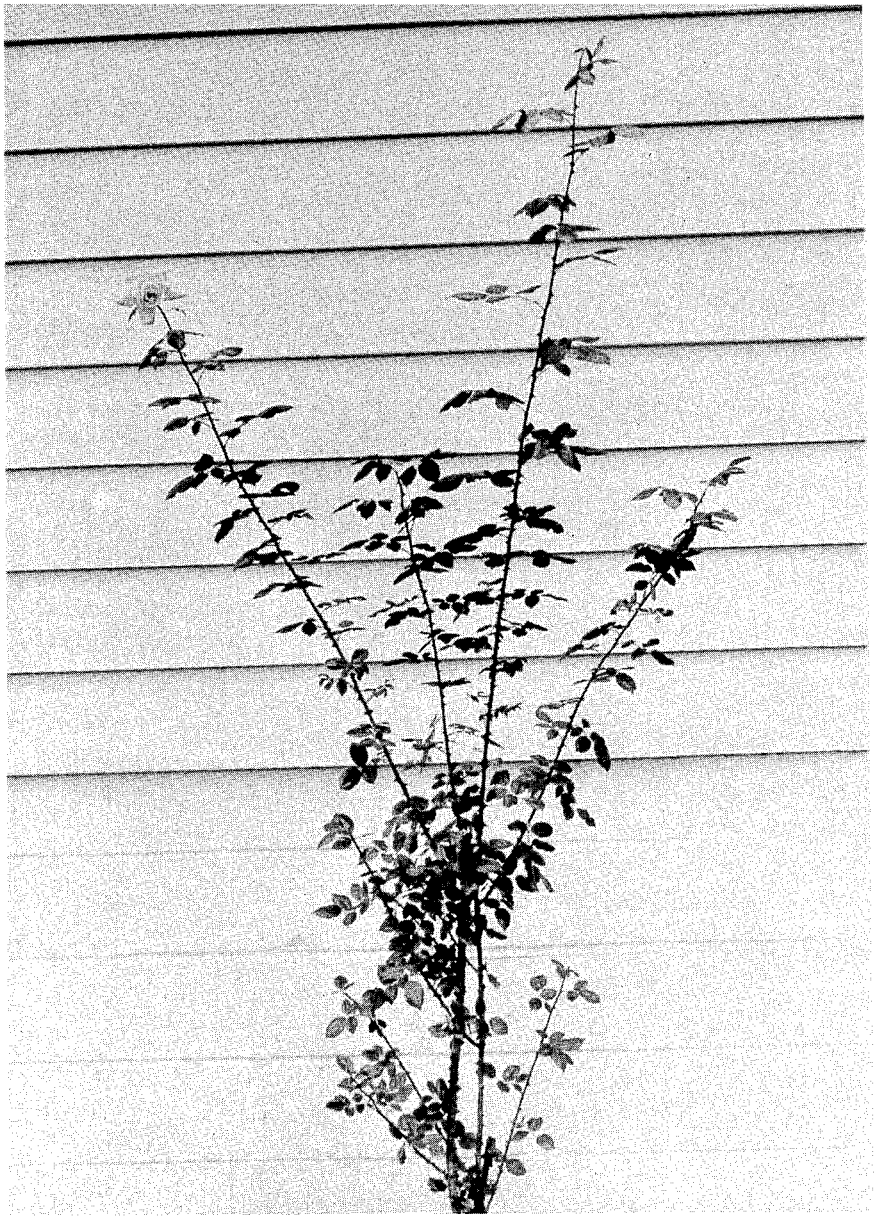
Inventor.
J. G. Valdrez
By: Robb & Robb
Attorneys.

United States Patent Office

Plant Pat. 1,660
Patented Nov. 12, 1957

1,660

ROSE PLANT

Jose Godoy Valdrez, Brentwood, Calif., assignor to Jackson & Perkins Company, Newark, N. Y., a corporation of New York Application March 19, 1957, Serial No. 647,175

1 Claim. (Cl. 47—61)

The present invention relates to a new and distinct variety of rose plant of the climbing hybrid tea class, which originated as a sport of the variety "Golden Masterpiece" (Plant Patent No. 1,284).

The new variety was discovered by me amongst a block of several thousand plants of "Golden Masterpiece" which were being grown in the fields of my assignee at Pleasanton, California. At the time of my discovery aforementioned, my attention was attracted to the same by the fact that one plant sent out long basal canes typical of a climbing characteristic, while all other plants in the field remained in the ordinary bush form corresponding to that of "Golden Masterpiece." Upon closer examination of the particular plant, I found that it had sported, and I thereupon took steps to preserve the sport, keep it under observation and later asexually reproduce the same. My observations and asexual reproductions, as performed by budding at Pleasanton, California, and also at Newark, New York, fully confirmed the climbing habit of the new sport and conclusively established that the climbing habit comes true to form and is transmissible through succeeding propagations.

In addition to the climbing habit of the new variety, which is evidenced by long climbing shoots attaining a height of from 8 to 10 feet, which bear flowers at the termination of the shoots, the new variety is further characterized by its short axillary flowering branches which bear flowers and foliage corresponding to those of its parent, "Golden Masterpiece," said flowers being Pinard Yellow, lightly overcast with Apricot Yellow, in general color tonality.

So far as I am aware, the parent variety, "Golden Masterpiece," has never exhibited a climbing habit, and its growth has been that of the average strong bush rose, while the new sport is differentiated therefrom by its vigorous and upright branching habit.

In view of the similarities in general characteristics between the new variety and its parent, except for the aforementioned distinctions, it is unnecessary to describe the new variety in detail, since it conforms substantially to the detailed description appearing in Plant Patent No. 1,284, dated June 15, 1954, to which reference may be readily had.

For convenience, the accompanying drawing shows in black-and-white a specimen plant of the new sport which is illustrative of the typical climbing habit of growth of the new variety.

I claim:

A new and distinct variety of rose plant of the climbing hybrid tea class, substantially as herein shown and described, characterized particularly as to novelty by its general similarity to its parent variety "Golden Masterpiece" (Plant Patent No. 1,284), but being essentially distinguished therefrom by its climbing habit of growth which is evidenced by long basal shoots which bear flowers at the terminal ends of the shoots, combined with short axillary flowering branches which bear flowers and foliage generally corresponding to those of the aforementioned parent variety.

No references cited.